US00PP21120P2

(12) United States Plant Patent
Klemm et al.

(10) Patent No.: US PP21,120 P2
(45) Date of Patent: Jun. 29, 2010

(54) ***XEROCHRYSUM* PLANT NAMED 'KLEBB08392'**

(50) Latin Name: *Xerochrysum bracteata*
Varietal Denomination: KLEBB08392

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/384,048

(22) Filed: Mar. 31, 2009

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L Bell
(74) *Attorney, Agent, or Firm*—Jondle & Associates, P.C.

(57) ABSTRACT

A new cultivar of *Xerochrysum* named 'KLEBB08392' particularly characterized by a very early flowering response, clear yellow inflorescences, stable and healthy foliage, and an upright, compact and harmonic growth habit, is disclosed.

1 Drawing Sheet

Genus and species: *Xerochrysum bracteata.*
Variety denomination: 'KLEBB08392'.

BACKGROUND OF THE NEW PLANT

The present invention comprises a new and distinct cultivar of *Xerochrysum*, botanically known as *Xerochrysum bracteata*(previously *Bracteantha bracteata*), and hereinafter referred to by the cultivar name 'KLEBB08392'. 'KLEBB08392' was discovered as a seedling resulting from a cross in Summer 2005 in Stuttgart, Germany between the proprietary female *Xerochrysum* parent, 'W 156' (unpatented) and the proprietary male *Xerochrysum* parent, 'W 007' (unpatented). A single plant selection was subsequently chosen for further evaluation and for asexual propagation.

The new cultivar was first propagated in May 2006 by vegetative cuttings in Stuttgart, Germany and has been asexually reproduced repeatedly by vegetative cuttings in Stuttgart, Germany over a two and one-half-year period (approximately 4 to 5 generations). 'KLEBB08392' has been found to retain its distinctive characteristics through successive asexual propagations.

Plant Breeder's Rights for this cultivar have been applied for in Canada on Mar. 31, 2008. 'KLEBB08392' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. A very early flowering response;
2. Clear yellow inflorescences;
3. Stable and healthy foliage; and
4. An upright, compact and harmonic growth habit.

DESCRIPTION OF THE PHOTOGRAPH

This new *Xerochrysum* plant is illustrated by the accompanying photograph which shows a close-up of the mature inflorescence. The colors shown are as true as can be reasonably obtained by conventional photographic procedures.

The photograph is of a plant about 4-months old and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEBB08392'. The data which define these characteristics were collected from asexual reproductions carried out in Stuttgart, Germany. The plant history was taken on 3-month old plants in 12-cm pots that were pinched once approximately 8 days after planting and grown in a greenhouse in April. The color readings were determined under natural light. Color references are to The R.H.S. Colour Chart of The Royal Horticultural Society of London (R.H.S.) (2001).

DESCRIPTION OF THE NEW PLANT

Classification:
- *Family.*—Asteraceae.
- *Genus and species.*—*Xerochrysum bracteata.*

Parentage:
- *Female parent.*—The proprietary *Xerochrysum* parent, 'W 156' (unpatented).
- *Male parent.*—The proprietary *Xerochrysum* parent, 'W 007' (unpatented).

Plant:
- *Form.*—Rounded, bushy.
- *Growth habit.*—Upright.
- *Propagation type.*—Vegetative cuttings.
- *Height* (*from soil level to top of the leaves without inflorescences*).—17.0 cm.
- *Diameter* (*area of spread*).—25.0 cm to 30.0 cm.
- *Time to initiate roots.*—8 days.
- *Time to produce a rooted cutting.*—18 days.
- *Root description and habit* (*immature plants*).—White, medium thickness, dense.
- *Time to produce a finished plant.*—9 weeks (63 days).

Branches:
*Type.*—Lateral branches.
*Quantity per plant.*—5 to 6 after pinching.
*Length.*—4.0 cm to 8.0 cm.
*Diameter.*—0.6 cm to 0.8 cm.
*Internode length.*—1.0 cm to 2.0 cm.
*Aspect.*—Round.
*Strength.*—Strong.
*Texture.*—Rough.
*Color.*—RHS 138A.

Leaves:
*Arrangement and type.*—Alternate.
*Length.*—4.0 cm to 8.0 cm.
*Width.*—1.4 cm.
*Shape.*—Lanceolate.
*Apex.*—Acute.
*Base.*—Blunt.
*Margin.*—Entire.
*Texture* (*both upper and lower surface*).—Rough.
*Venation pattern.*—Pinnate.
*Venation color* (*both upper and lower surface*).—RHS 137D.
*Color.*—Upper surface (both immature and mature): RHS 138A. Lower surface (both immature and mature): RHS 138C.
*Petiole.*—Absent.

Inflorescence:
*Appearance.*—Single and dichasium.
*Flowering habit and timing.*—Continuous from Spring to Fall.
*Quantity of inflorescences on the plant.*—6 to 10.
*Fragrance.*—Absent.
*Lastingness of inflorescences on the plant.*—About 14 to 26 days.
*Diameter.*—About 5.0 cm to 7.0 cm.
*Depth* (*height*).—4.0 cm to 6.0 cm.
*Disc diameter.*—4.5 cm.
*Receptacle diameter.*—About 1.0 cm.
*Receptacle height.*—About 0.6 cm.

Bud:
*Height.*—0.6 cm to 0.9 cm.
*Diameter.*—0.8 cm.
*Shape.*—Fircone-shaped, elliptic.
*Color.*—Between RHS 23C and RHS 23D.

Involucral bracts:
*Shape.*—Elliptic.
*Length, largest bracts.*—1.0 cm to 1.5 cm.
*Width, largest bracts.*—0.3 cm to 0.5 cm.
*Apex.*—Acute.
*Base.*—Attenuate.
*Margin.*—Entire.
*Texture.*—Rough.
*Number of involucral bracts per inflorescence.*—Varies.
*Color* (*when opening and when fully opened*).—Upper surface: RHS 7A. Lower surface: RHS 7A.

Disc florets:
*Arrangement.*—Massed in the center of the receptacle.
*Shape.*—Longish, small, tubular.
*Apex.*—Obtuse.
*Length.*—0.2 cm.
*Diameter, apex.*—0.04 cm.
*Diameter, base.*—0.04 cm.
*Number of disc florets per inflorescence.*—Greater than 50.
*Color.*—Immature: RHS 7B. Mature: RHS 23A. Apex: RHS 23A. Mid-section: RHS 23A. Base: RHS 23B.

Phyllaries:
*Quantity per inflorescence.*—8 to 10.
*Length.*—0.4 cm.
*Width.*—0.4 cm.
*Shape.*—Elliptic.
*Apex.*—Acute.
*Base.*—Obtuse.
*Margin.*—Entire.
*Texture* (*both the upper and lower surfaces*).—Smooth.
*Color.*—Upper surface: RHS 137B. Lower surface: RHS 137B.

Peduncles:
*Length.*—6.0 cm to 7.0 cm.
*Diameter.*—0.3 cm to 0.6 cm.
*Strength.*—Strong.
*Aspect.*—Erect.
*Texture.*—Rough.
*Color.*—RHS 137D Reproductive organs: Unable to determine reproductive organs due to small size.

Fruit and seed set: None observed.

Disease and insect resistance: No common diseases and insects observed.

COMPARISON WITH PARENTAL AND COMMERCIAL CULTIVARS

'KLEBB08392' differs from the female parent, the proprietary *Xerochrysum* 'W 156' (unpatented) in that 'KLEBB08392' has clear yellow inflorescences, small leaves, firm foliage and a compact growth habit, while 'W 156' has yellow-orange inflorescences, weak foliage and a strong growth habit.

'KLEBB08392' differs from the male parent, the proprietary *Xerochrysum* 'W 007' (unpatented) in that 'KLEBB08392' has clear yellow inflorescences, firm foliage and a compact growth habit, while 'W 007' has lemon-colored inflorescences, very firm foliage and a strong growth habit.

'KLEBB08392' differs from the commercial comparison variety 'KLEBA04076' (U.S. Plant Pat. No. 17,915) in that 'KLEBB08392' has clear yellow inflorescences, a very early flowering response and small, healthy leaves, while 'KLEBA04076' has dark yellow inflorescences, a medium to early flowering response and wider, weak leaves.

I claim:

1. A new and distinct cultivar of *Xerochrysum* plant named 'KLEBB08392' as shown and described herein.

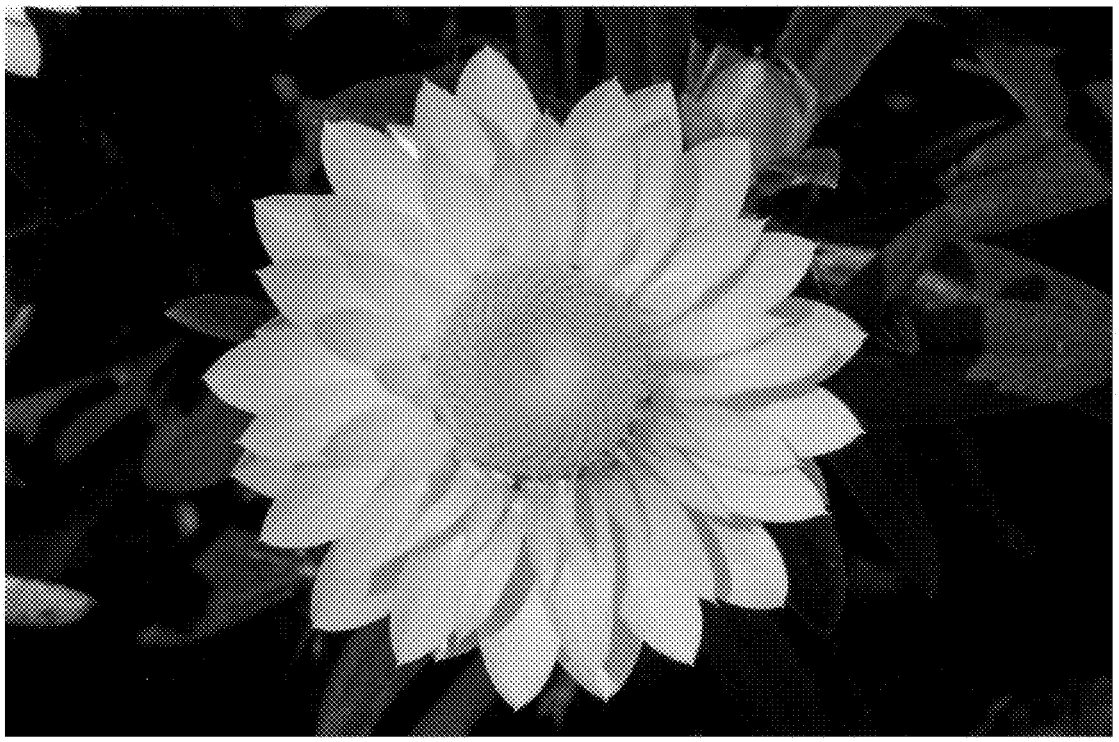

* * * * *